(12) United States Patent
Moeskops et al.

(10) Patent No.: US 10,022,188 B2
(45) Date of Patent: Jul. 17, 2018

(54) HAIR REMOVING LASER SHAVER

(71) Applicant: KONINKLIJKE PHILIPS ELECTRONICS N.V., Eindhoven (NL)

(72) Inventors: Bastiaan Wilhelmus Maria Moeskops, Uden (NL); Mark Thomas Johnson, Arendonk (BE); Rieko Verhagen, Vught (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 623 days.

(21) Appl. No.: 14/366,550

(22) PCT Filed: Dec. 11, 2012

(86) PCT No.: PCT/IB2012/057171
§ 371 (c)(1),
(2) Date: Jun. 18, 2014

(87) PCT Pub. No.: WO2013/098685
PCT Pub. Date: Jul. 4, 2013

(65) Prior Publication Data
US 2015/0133903 A1 May 14, 2015

(30) Foreign Application Priority Data

Dec. 27, 2011 (EP) .................................. 11195740

(51) Int. Cl.
A61B 18/20 (2006.01)
A61B 18/00 (2006.01)
(Continued)

(52) U.S. Cl.
CPC ........ *A61B 18/203* (2013.01); *B23K 26/0643* (2013.01); *B26B 19/048* (2013.01);
(Continued)

(58) Field of Classification Search
None
See application file for complete search history.

(56) References Cited

U.S. PATENT DOCUMENTS 4,473,074 A * 9/1984 Vassiliadis ........... A61B 18/201
219/121.74
5,182,857 A 2/1993 Simon
(Continued)

FOREIGN PATENT DOCUMENTS

EP 2189129 A1 5/2010
WO 9106406 A1 5/1991
(Continued)

*Primary Examiner* — Gary Jackson
*Assistant Examiner* — Qingjun Kong

(57) ABSTRACT

A shaver is disclosed that comprises a handle (12) and a cutting head (13) that are arranged to move relative to each other via a rotational and/or translational axis (16,17). This movement facilitates skin contour following during shaving to achieve a close cut. The handle (12) comprises a laser source that emits a laser beam and the shaver has an optical system that includes optical elements (23,25,26,37,40,42) to direct a part of a laser beam so that it coincides with the rotational axis and/or is parallel to the translational axis. In this way, when the cutting head (13) is moved the optical alignment between the laser source, optical elements (23, 25,26,37,40,42) and cutting zone (28) does not change.

4 Claims, 4 Drawing Sheets

(51) Int. Cl.
  *B26B 19/40* (2006.01)
  *B26B 19/38* (2006.01)
  *B26B 19/04* (2006.01)
  *B23K 26/06* (2014.01)

(52) U.S. Cl.
  CPC .......... *B26B 19/3873* (2013.01); *B26B 19/40* (2013.01); *A61B 2018/00476* (2013.01)

(56) References Cited

U.S. PATENT DOCUMENTS

| | | | |
|---|---|---|---|
| 5,993,440 A * | 11/1999 | Ghassemi | B26B 19/00 30/41.5 |
| 6,533,775 B1 | 3/2003 | Rizoiu | |
| 7,479,137 B2 | 1/2009 | Yamazaki et al. | |
| 2004/0237310 A1 * | 12/2004 | Shiba | B26B 19/048 30/43.92 |
| 2005/0049657 A1 | 3/2005 | Jay | |
| 2009/0240243 A1 | 9/2009 | Brottier | |

FOREIGN PATENT DOCUMENTS

| | | | | |
|---|---|---|---|---|
| WO | 9216338 A1 | 10/1992 | | |
| WO | WO 9216338 A1 * | 10/1992 | ........... | A61B 18/203 |
| WO | 9533600 A1 | 12/1995 | | |
| WO | WO 9533600 A1 * | 12/1995 | ............ | B26B 19/38 |
| WO | 2007039854 A1 | 4/2007 | | |
| WO | 2008050261 A1 | 5/2008 | | |
| WO | 2009081301 A1 | 7/2009 | | |
| WO | 2009109885 A2 | 9/2009 | | |

* cited by examiner

HAIR REMOVING LASER SHAVER

CROSS-REFERENCE TO PRIOR APPLICATIONS

This application is the U.S. National Phase application under 35 U.S.C. § 371 of International Application No. PCT/IB2012/057171, filed on Dec. 11, 2012, which claims the benefit of European Patent Application No. EP11195740.3, filed on Dec. 27, 2011. These applications are hereby incorporated by reference herein.

FIELD OF THE INVENTION

This invention relates to a shaver for cutting hair.

BACKGROUND

It is known to provide a shaver or razor that relies on a laser for cutting hair rather than an arrangement of cutting blades. Shavers without blades have fewer moving parts and so wear is reduced, which provides an advantage over mechanical shavers. Furthermore, the use of a laser can reduce skin irritation as there are no sharp objects to contact the skin surface.

Laser shavers work by optical absorption in which hair exposed to a laser beam absorbs the energy of the beam, causing it to be vaporised and/or severed.

Shaving performance is typically measured by two criteria—closeness of shave and irritation of the skin. Laser shavers are inherently good performers with respect to irritation because there are no cutting elements that contact the skin. However, closeness of cut is important and skin contour following is necessary to achieve a consistently close cut and minimise stubble. A mechanical shaver is typically provided with a moveable shaving head to enable it to move relative to a handle so that the head follows the contours of the skin to which the head is applied. A moveable cutting head can be mounted so that it can rotate with respect to the main body or handle of the shaver and/or so that it can translate linearly in a direction towards and away from the handle so that a substantially constant pressure of the cutting head against the skin is maintained. The head may be attached to the handle via a spring mount to bias the shaving head towards a default or neutral position that the head assumes when it is not pressed against the user's skin.

It is known from WO 92/16338 and U.S. Pat. No. 5,993,440 to provide a shaver that employs a laser to cut hair and which uses reflective elements to direct a laser beam into a cutting zone where it extends adjacent and substantially parallel to the skin surface and cuts hairs as they move through the cutting zone. However, the shavers known from both these documents are of the fixed head type and do not follow the contours of the skin.

SUMMARY OF THE INVENTION

This invention seeks to overcome or substantially alleviate the problems referred to above and to provide a laser shaver that cuts hairs by optical absorption and which is capable of following contours of the skin. The invention seeks to achieve a satisfactory cutting length by including a cutting head that is moveable, i.e. rotatable and/or translational, with respect to the main body or handle of the shaver whilst maintaining optical alignment of the laser within the device.

According to the invention, there is provided a shaver comprising a handle having a cutting head mounted to the handle arranged to rotate relative to the handle about a rotational axis such that the cutting head follows the contours of the skin during use, a laser beam generator in the handle and an optical system for directing a laser beam emitted by the generator into the cutting head for cutting hair, said optical system being configured so that a portion of the optical axis of the laser beam emitted by the generator is co-incident with said rotational axis about which the cutting head rotates relative to the handle.

According to another aspect of the invention, there is provided a shaver comprising a handle having a cutting head mounted to the handle arranged to move linearly relative to the handle along a translational axis such that the cutting head follows the contours of the skin during use, a laser beam generator in the handle and an optical system for directing a laser beam emitted by the generator into the cutting head for cutting hair, said optical system being configured so that a portion of the optical axis of the laser beam emitted by the generator is parallel to said translational axis along which the cutting head translates relative to the handle.

In a preferred embodiment, the cutting head is moveable relative to the handle about the rotational axis and along the translational axis, a portion of the optical axis of the laser beam being coincident with the rotational axis, a portion of the optical axis also being parallel to the translational axis.

As the cutting head moves relative to the handle, it follows the contours of the skin during shaving to achieve a close cut. As the laser beam is directed so that it coincides with the axis of movement of the head the optical alignment between the laser source and the reflective elements does not change despite movement of the cutting head relative to the handle. As the cutting head can move toward or away from the user's skin during shaving, the pressure of the shaver against the skin can be controlled.

Preferably, the means for directing the laser beam comprises a first optical element lying on said rotational axis and fixed relative to the handle for directing a laser beam emitted from the laser generator in a direction along the rotational axis. As the optical element lies on the rotational axis, the beam can be directed along the optical axis before being redirected into the cutting head. Therefore, the angular orientation of the cutting head relative to the handle has no effect on the optical axis and the laser beam is still directed along the same path within the cutting head.

The means for directing the laser beam may comprise a second optical element lying on the rotational axis and fixed relative to the cutting head for directing a laser beam coincident with the optical axis into the cutting head.

The cutting head preferably comprises a cutting zone that receives hairs to be cut when the shaver is in use and said optical system comprises a third optical element in the cutting head, said third optical element being positioned to direct the laser beam from the second optical element into the cutting zone. As the laser beam is directed along the rotational axis, a second optical element directs the beam away from the optical axis and into the cutting head, from where it can be further redirected by a third optical element into a cutting zone to cut hair received in said zone.

The cutting head may comprise a cutting zone that receives hairs to be cut when the shaver is in use and at least one optical element is positioned in the cutting head to direct the laser beam into the cutting zone. As the optical axis extends parallel to the translational axis between the handle and the cutting head, movement of the cutting head away, or towards, the handle has no effect on the direction of the laser beam which is still directed into a cutting zone to cut hair received in said zone, the only difference being that the laser beam travels a slightly greater distance between reflectors when the cutting head has been translated further away from the handle than when it is translated in a direction towards the handle.

The optical system preferably includes at least one optical element received in the handle for redirecting a laser beam emitted by the laser generator in a direction along the translational axis.

In any embodiment, the optical element(s) may comprise reflectors to reflect the laser beam.

In either embodiment, the shaver comprises a comb, lamella, blunt blade, refractor, stretcher, lubrastrip etc. to manipulate hairs into the cutting zone as the shaver is moved over the skin.

In another embodiment, the handle may include multiple laser generators that emit laser beams along separate optical axes, each laser beam being directed into the cutting head for cutting hair.

BRIEF DESCRIPTION OF THE DRAWINGS

Preferred embodiments will now be described, by way of example only, with reference to the drawings in which.

DETAILED DESCRIPTION

A shaver that uses a laser for cutting hair relies on the accurate alignment of the laser source, optical components such as lenses, reflective elements and other components to ensure that the laser beam is accurately directed into the cutting plane. Any slight misalignment will result in reduced cutting effectiveness and may expose skin to the laser beam which may cause discomfort. Movement of a cutting head with respect to the main body or handle of a shaver, in which the laser generator is located, makes it difficult to ensure continuous and accurate alignment of the components, although movement of the cutting head is desirable to ensure that it closely follows the contours of a user's skin.

Figure 1:
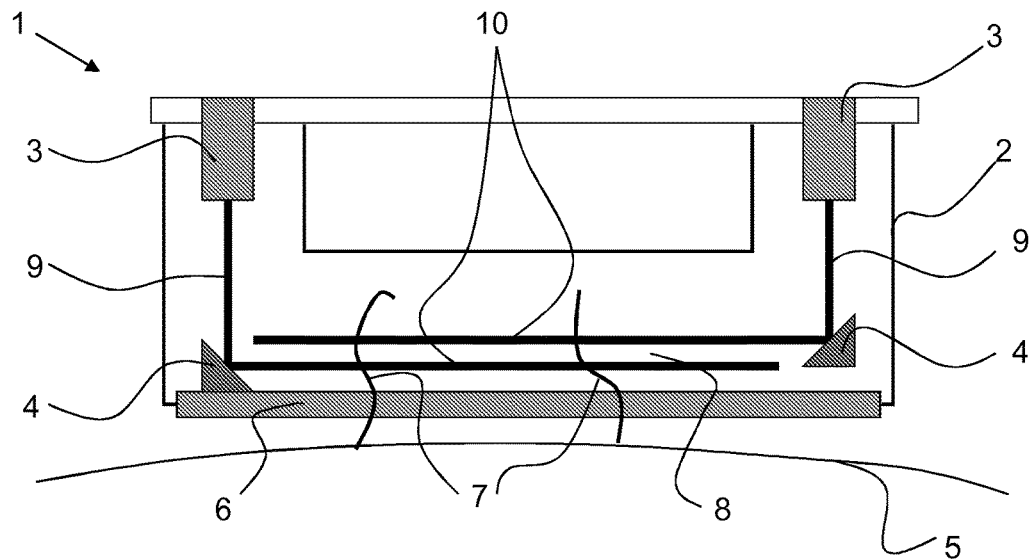
FIG. 1 shows a shaver head that employs a laser to cut hair, as is known in the art.

Referring to the drawings, FIG. 1 shows a schematic diagram of a laser shaver 1 that is known in the art. The laser shaver comprises a body 2, two laser sources 3 and two reflective elements 4. Only the cutting head of the body 2 is shown, although this shaver also includes a handle that rigidly attaches to the cutting head to allow a user to hold and move the cutting head over the skin 5.

The cutting head comprises a comb 6 that manipulates hairs 7 into a cutting zone 8 as the shaver 1 is moved over the skin 5. Instead of, or in addition to a comb the cutting head may also comprise a lamella, blunt blade, retractor, stretcher or lubrastrip. All are known from existing shavers for manipulating hairs or providing lubrication between the shaver and the skin. The laser sources 3 are located on opposite sides of the cutting head and each source directs a laser beam 9 towards the reflective elements 4 that are positioned to reflect the beam 9 through 90 degrees and across a cutting zone 8 that is adjacent to the comb 6. In this way, the hairs 7 are exposed to the laser beams 10 as they pass through the cutting zone 8 and the hairs 7 are cut by optical absorption. The reflective elements 4 are positioned so that there are two cutting beams 10 that cut the hairs 7 at different lengths; one reflective element is located further away from the comb 6 than the other. It is also possible to position the laser sources 3 and reflective elements 4 so that the two cutting beams 10 are at the same height but adjacent to each other in the cutting zone 8, so that two laser beams 10 cut the hairs 7 to the same length in two different positions.

Figure 2:
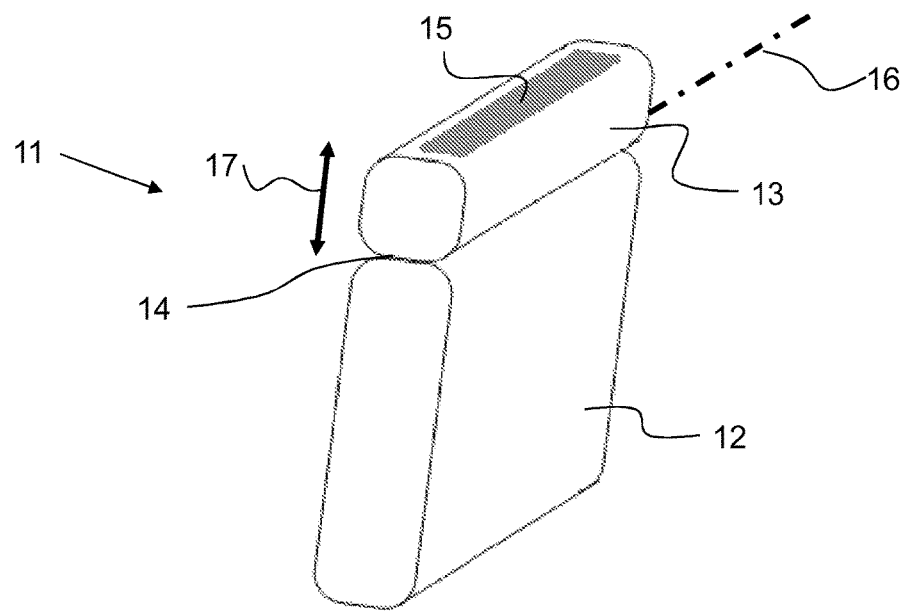
FIG. 2 shows a simplified perspective view of a shaver comprising a cutting head and a handle rotatably mounted to each other, according to an embodiment of the invention.

FIG. 2 shows a simplified view of a shaver 11 according to an embodiment of the invention and which comprises a handle 12 and a cutting head 13 that are joined by a connecting portion 14 such as a hinge so that the cutting head 13 can pivot relative to the handle 12. The cutting head 13 comprises a cutting zone 15 in which hair is received when the shaver 11 is in use. The connecting portion 14 allows the cutting head 13 to pivot relative to the handle 12, so that as the cutting head 13 is moved across the skin it follows the contours of the skin which is useful for achieving a satisfactory cutting length and to minimise stubble. The cutting head 13 should be able to follow the contours of the skin regardless of the pressure, velocity or skin friction that is present.

Figure 3:
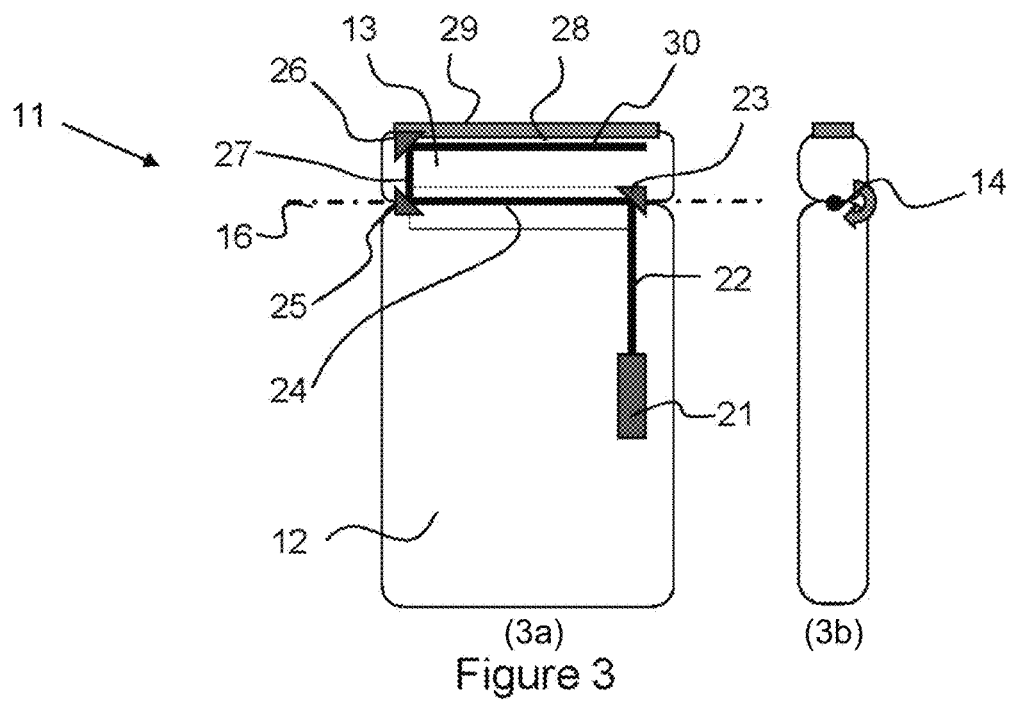
FIG. 3 shows front and side views (3a) and (3b), respectively, of the shaver of FIG. 2, including lines showing the optical path from the laser generator to a cutting zone.

The rotational connection between the cutting head 13 and the handle 12 better enables the cutting head 13 to follow the contours of the skin. The laser generator is located in the handle 12 and, as explained in more detail below, optical alignment is maintained through the rotational connection between the cutting head and the handle. FIG. 3 shows a further view of the shaver 11 shown in FIG. 2. The handle 12 comprises a laser generator 21 that emits a laser beam 22 towards the cutting head 13 and includes collimation and focusing optics (not shown). The shaver 11 comprises an optical system that comprises optical elements, such as reflectors including dielectric mirrors, metal mirrors or prisms that work by total internal reflection or any other type of reflection, and are large enough to accommodate the laser beam. A first reflector 23 is fixed to the handle 12 and is positioned to receive the laser beam 22 from the laser generator 21 and redirect it through 90 degrees so that the redirected laser beam 24 coincides with the rotational axis 16. A second reflector 25 is fixed to the cutting head 13 and is also positioned on the rotational axis 16, spaced from the first reflector 23. The second reflector 25 receives the laser beam 24 that is coincident with the rotational axis 16, having been reflected from the first reflector 23. The second reflector 25 reflects the laser beam through 90 degrees into the cutting head 13 where a third reflector 26 is positioned to receive the reflected laser beam 27 and redirect it across the cutting zone 28, adjacent to a comb 29 on the head portion 13, so that any hairs that are in the cutting zone 28 are cut by the laser beam 30.

The first reflector 23 is fixed to the handle 12 so that it does not move when the cutting head 13 rotates and the laser beam 22 is consistently received from the laser source 21 and reflected along the rotational axis 16. The second reflector 25 is fixed to the cutting head 13 and rotates about the rotational axis 16 when the cutting head 13 rotates. This ensures that the reflected laser beam 27 is consistently reflected from the second reflector 25 towards the third reflector 26, also fixed to the cutting head 13, and subsequently into the cutting zone 28. In this way, the laser beam 24 and the rotational axis 16, between the first and second reflectors 23, 25, always coincide. If the laser beam 24 did not coincide with the rotational axis 16 then the reflectors 23, 25, 27 would become misaligned as a result of rotation of the cutting head 13 relative to the handle 12 and the laser would not reach the cutting zone 28 or it would be misaligned in the cutting zone.

The first and second reflectors should be positioned as close together as possible so that the optical alignment of the reflectors with the rotational axis becomes less critical. It is more challenging to maintain optical alignment over a larger distance, so the first and second reflectors should be positioned as close as possible taking into account the mechanical limitations such as the size of reflective elements and the maximum angle of rotation.

Figure 4:
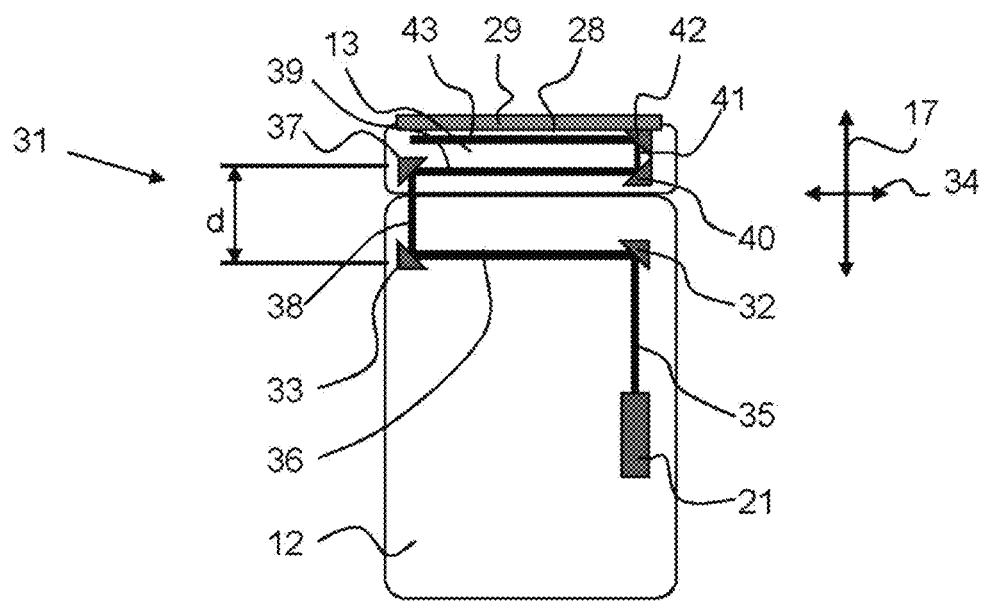
FIG. 4 shows a second embodiment of a shaver according to an embodiment of the invention which also comprises a cutting head and a handle but in which the cutting head is moveable linearly in a direction away from and towards the handle.

FIG. 4 shows a second embodiment of the laser shaver 31 comprising a cutting head 13 and a handle 12. In this embodiment, the connection 14 between the handle 12 and the cutting head 13 is such that the cutting head 13 can move linearly along a translational axis 17 (in the direction of arrow 'd' in FIG. 4) in a direction towards or away from the handle 12. The connection 14 could be a mechanism (not shown) of guiding rails or slides with springs to ensure that the cutting head 13 returns to a neutral position when not subject to any force that results from pushing the cutting heat 13 against the skin.

The handle 12 comprises a laser generator 21 and first and second reflectors 32, 33 which are arranged so that the optical axis or path is aligned with a plane parallel to the translational axis 17, at least where the laser beam passes between the handle 12 and the cutting head 13. Within the handle 12 and/or cutting head 13, the beam may also be directed along a lateral axis 34, which is perpendicular to the translational axis 17. The laser generator 21 irradiates a beam 35 in the direction of the cutting head 13 and the first reflector 32 is positioned to receive that laser beam 35 and redirect it through 90 degrees into a lateral direction across the handle 12. The second reflector element 33 is positioned opposite the first reflector 32, in the same plane, and redirects the laser beam 36 through 90 degrees into the cutting head 13.

The cutting head 13 comprises a third reflector 37 that is positioned to receive the laser beam 38 from the second reflector 33. The third reflector element 37 redirects the light in the lateral direction 34 towards a fourth reflector 40 that is positioned to receive this beam 39. The fourth reflector 40 is positioned to redirect the beam 39 into the translational direction towards a fifth reflector 42 that reflects the beam 41 across the cutting zone 28, adjacent to the comb 29, so that when hairs enter the space in the comb 29 they are cut by exposure to the laser beam 43.

When the cutting head 13 slides relative to the handle 12, in the translational direction 17, the distance 'd' between the second and third reflectors 33, 37 is altered. This has no effect on the alignment of the laser beam 38 with the reflectors 33, 37 so long as the portion of the laser beam 38 between the second and third reflectors 33, 37 and the translational axis 17 of movement of the head portion 13 are parallel. So the cutting head 13 slides relative to the handle 12 without affecting the optical alignment.

Figure 5:
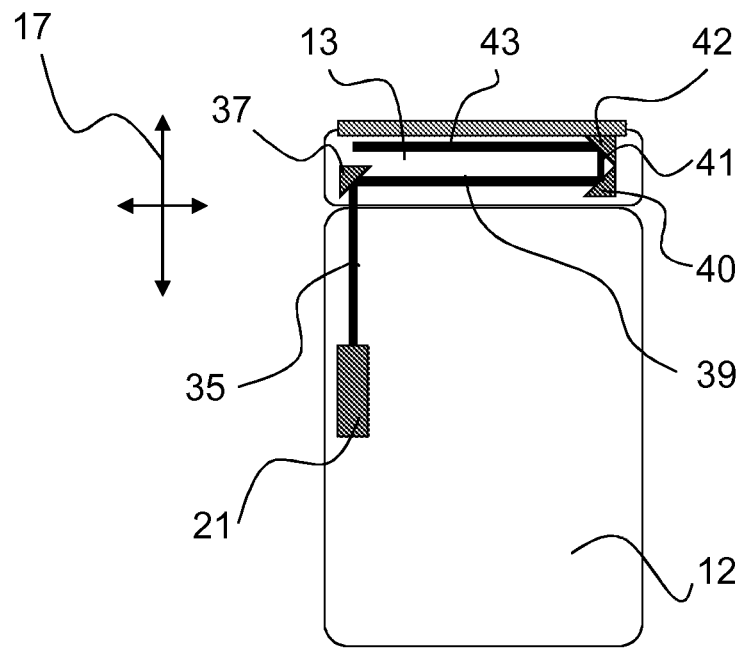
FIG. 5 shows an alternative optical arrangement for translational connection between the handle and cutting head.

FIG. 5 shows a simplified embodiment of the shaver 31 described with reference to FIG. 4. This shaver 31 does not comprise reflectors located in the handle 12 so that the laser beam 35 that is emitted from the laser generator 21 travels directly to the third reflector 37, located in the cutting head 13, which then reflects the beam 35 towards a fourth 40 and then fifth reflector 42 positioned as they were in the previous embodiment. This reduces the number of components required and also any losses in beam intensity that may result from the reflections.

Movement of the cutting head 13 relative to the handle 12 alters the distance between the laser generator 21 and the third reflector 37. This movement does not effect the alignment of the laser beam 35 and reflectors.

Figure 6:
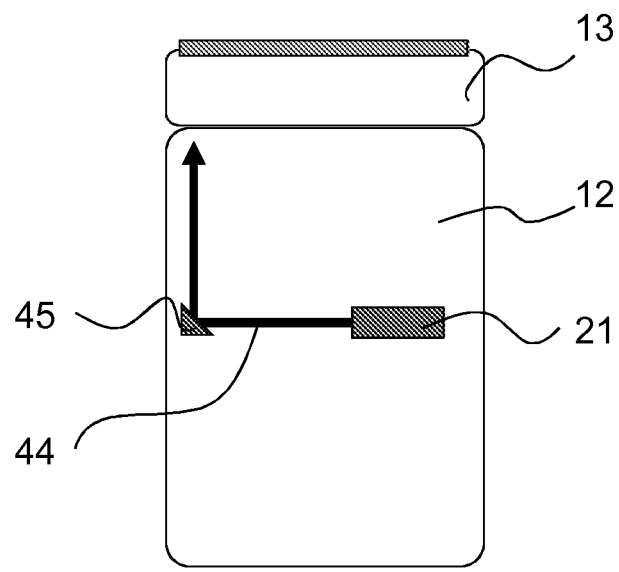
FIG. 6 shows an alternative orientation for the laser source.
Figure 7:
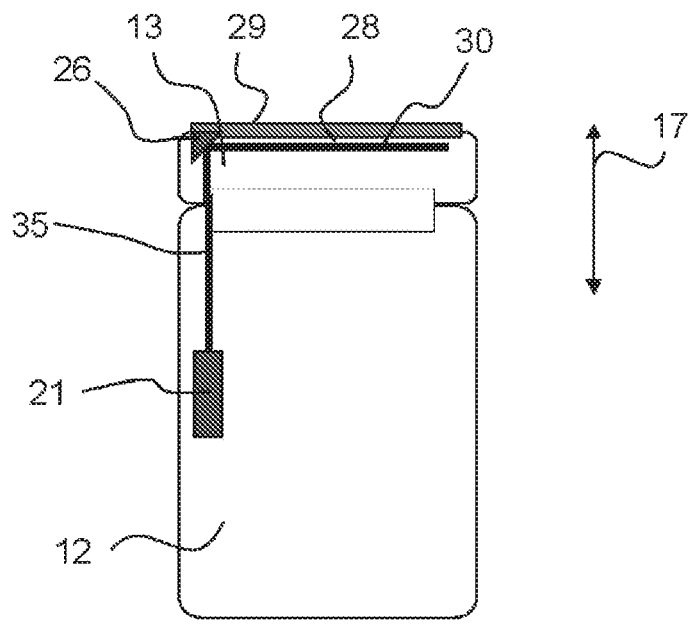
FIG. 7 shows another alternative optical arrangement for translational connection between the handle and cutting head.

FIG. 6 shows an alternative laser source arrangement whereby the laser generator 21 is positioned perpendicularly to the configurations that have previously been described. The laser generator 21 emits a laser beam 44 in a lateral direction and the beam 44 is reflected towards the cutting head 13 by a reflector 45. Further reflectors can then be arranged as previously described, depending on whether the cutting head is mounted for rotation or translation relative to the handle. FIG. 7 shows another alternative laser source and reflector arrangement.

This is a similar embodiment to that described with reference to FIG. 5, but with fewer components in the optical system and therefore fewer components to optically align. In this embodiment the cutting head 13 can move linearly with respect to the handle 12 along a translational axis 17. The shaver comprises a laser source 21 located in the handle 12 and a reflector 26 positioned to a side of the cutting zone 28, aligned with the laser beam 35. The reflector 26 directs the laser beam 35 across the cutting zone 28 so that any hairs present in the cutting zone are severed. Movement of the cutting head 13 with respect to the handle, along the translational axis 17, changes the distance between the reflector 26 and the laser source 21. The optical axis of the laser beam between the laser source 21 and the first reflector 26 is parallel to the translational axis 17. Therefore, the optical alignment of the laser source 21 and the reflector 26 is unaffected during movement of the cutting head.

Figure 8:
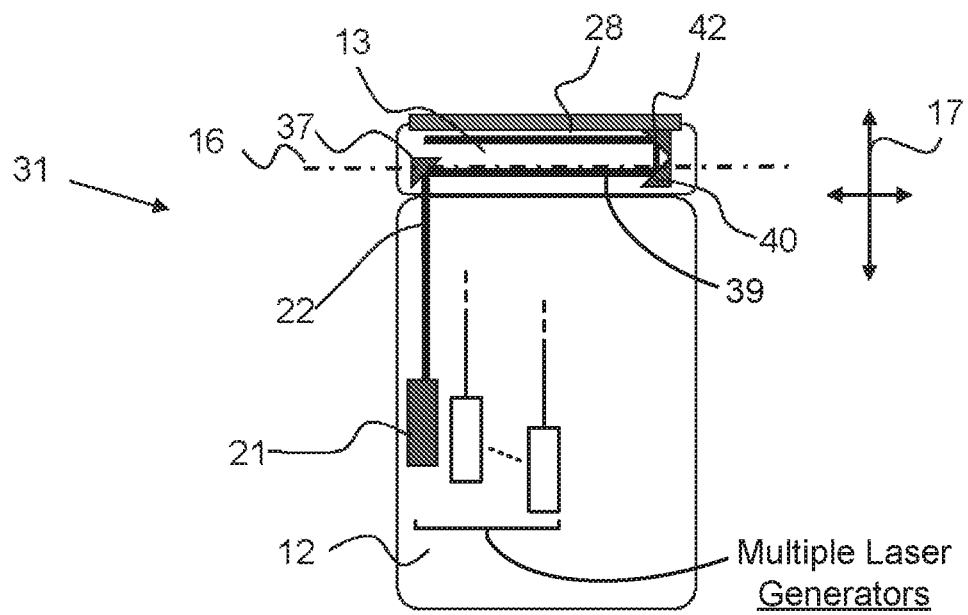
FIG. 8 shows an optical arrangement for translational and rotational connection between the handle and cutting head.

FIG. 8 shows an embodiment of a laser shaver 31 with a cutting head 13 that is moveable both rotationally and in a translational direction with respect to the handle 12. The cutting head 13 rotates about the rotational axis 16 and translates along the axis 17. A laser source 21 is located in the handle 12 and directs a laser beam 22 towards and into the cutting head 13. A first reflector 37 is positioned in the cutting head 13 in line with the rotational axis 16 and is connected to the cutting head 13 so that it moves in the translational direction with the cutting head 13, but does not rotate when the cutting head 13 rotates. The reflector 37 intercepts the laser beam 22 from the laser source 21 and directs it coincidentally along the rotational axis 16. The portion of the laser beam 39 that is coincidental with the rotational axis 16 is intercepted by a second reflector 40 which directs the laser beam towards the cutting zone 28 where a third reflector 42 directs the laser beam across the cutting zone 28 to sever hairs. The second and third reflectors are rigidly attached to the cutting head 13 so that they rotate and move when the cutting head 13 does, maintaining optical alignment for all positions of the cutting head.

The combination of rotation and translation of the cutting head 13, with respect to the handle 12, gives improved contour following performance and increases the effectiveness of the shaver.

Each laser generator 21 may comprise a laser diode, diode pumped solid state (DPSS) device, optical parametric oscillator (OPO) device or any other source of coherent light. Multiple cutting laser beams may be simultaneously used in different planes and this may require multiple laser sources (e.g., as illustrated in FIG. 8 via multiple laser generators that emit laser beams along separate optical axes, each laser beam being directed into the cutting head for cutting hair). It is also possible to only use one laser source to create multiple cutting beams if a beam splitter is used to create two beams that can be directed by reflective elements to create two cutting beams. Furthermore, the cutting beams may be re-directed by a further reflective element, after they have already passed through the cutting zone, back into the cutting zone to create multiple cutting beams. It will be appreciated that the term "comprising" does not exclude other elements or steps and that the indefinite article "a" or "an" does not exclude a plurality. The mere fact that certain measures are recited in mutually different dependent claims does not indicate that a combination of these measures cannot be used to an advantage. Any reference signs in the claims should not be construed as limiting the scope of the claims.

Although claims have been formulated in this application to particular combinations of features, it should be understood that the scope of the disclosure of the present invention also includes any novel features or any novel combinations of features disclosed herein either explicitly or implicitly or any generalisation thereof, whether or not it relates to the same invention as presently claimed in any claim and whether or not it mitigates any or all of the same technical problems as does the parent invention. The applicants hereby give notice that new claims may be formulated to such features and/or combinations of features during the prosecution of the present application or of any further application derived therefrom.

Other modifications and variations falling within the scope of the claims hereinafter will be evident to those skilled in the art.

The invention claimed is:

1. A shaver comprising:
   a handle;
   a laser beam cutting head mounted to the handle via a rotational connection and arranged to rotate relative to the handle about a single rotational axis such that the laser beam cutting head follows contours of a user's skin during use;
   a laser beam generator disposed in the handle; and
   an optical system for directing a laser beam emitted by the laser beam generator into the laser beam cutting head for cutting hair, wherein said optical system is configured to (i) render a portion of an optical axis of the laser beam emitted by the laser beam generator coincident with the rotational axis about which the laser beam cutting head is rotatable relative to the handle and (ii) maintain an optical alignment of the laser beam through the rotational connection between the laser beam cutting head and the handle for all rotational positions up to a maximum angle of rotation of the laser beam cutting head,
   wherein the optical system comprises (i) a first optical element rigidly attached to the handle and positioned on the rotational axis for directing the laser beam emitted from the laser generator along the rotational axis, (ii) a second optical element rigidly attached to the laser beam cutting head and positioned on the rotational axis for directing a laser beam coincident with the rotational axis into the laser beam cutting head, and (iii) a third optical element rigidly attached in the laser beam cutting head, said third optical element being positioned to reflect the laser beam from the second optical element into a cutting zone of the laser beam cutting head that receives hairs to be cut when the shaver is in use.

2. The shaver according to claim 1, wherein the first optical element comprises a reflector.

3. The shaver according to claim 1, further comprising one or more of a comb, lamella, blunt blade, retractor, stretcher and lubrastrip to manipulate hairs into the cutting zone as the cutting head is moved over the skin.

4. The shaver according to claim 1, further comprising multiple laser generators disposed in the handle that emit laser beams along separate optical axes, each laser beam being directed into the cutting head for cutting hair.

* * * * *